United States Patent
Chen et al.

(10) Patent No.: US 8,110,675 B2
(45) Date of Patent: Feb. 7, 2012

(54) TP EXPRESSION-INHIBITING COMPOUND AND SIRNA SEQUENCE THEREOF

(75) Inventors: Lih-Chyang Chen, Xindian (TW); Yu-Sun Chang, Linkou Township, Taipei County (TW)

(73) Assignee: Chang Gung University, Tao-Yuan (TW)

( * ) Notice: Subject to any disclaimer, the term of this patent is extended or adjusted under 35 U.S.C. 154(b) by 316 days.

(21) Appl. No.: 12/484,858

(22) Filed: Jun. 15, 2009

(65) Prior Publication Data
US 2010/0317839 A1   Dec. 16, 2010

(51) Int. Cl.
C07H 21/02   (2006.01)
C07H 21/04   (2006.01)
A61K 31/70   (2006.01)
C12Q 1/68    (2006.01)

(52) U.S. Cl. .................... 536/24.5; 536/23.1; 536/24.1; 514/44 A

(58) Field of Classification Search .................. None
See application file for complete search history.

(56) References Cited

U.S. PATENT DOCUMENTS 7,678,897 B2 * 3/2010 McSwiggen et al. ........ 536/24.5

OTHER PUBLICATIONS

Irene Pino, Rliben Pio, Gemma Toledo, Natalia Zabalegui, Silvestre Vicent, Natalia Rey, Maria D. Lozano, Wenceslao Torree, Jesu's Garcia'A-Foncillasd, Luis M. Montuenga, "Altered patterns of expression of members of the heterogeneous nuclear ribonucleoprotein (hnRNP) family in lung cancer". p. 131-143 Lung Cancer (2003).

Ryuji Ikeda, Xiao-Fang Che, Mina Ushiyama, Tatsuya Yamaguchi, Hiroshi Okumura, Yuichi Nakajima, Yasuo Takeda, Yoshihiko Shibayama, Tatsuhiko Furukawa, Masatatsu Yamamoto, Misako Haraguchi, Tomoyuki Sumizawad, Katsushi Yamada, Shin-Ichi Akiyama, "2-Deoxy-D-ribose inhibits hypoxia-induced apoptosis by suppressing the phosphorylation of p38 MAPK". p. 280-285, Biochemical and Biophysical Research Communications 342 (2006).

P. Roychoudhury and K Chaudhuri "Evidence for heterogeneous nuclear ribonucleoprotein K overexpression in oral squamous cell carcinoma" British Journal of Cancer (2007) 97, p. 574-575.

Karol Bomsztyk, Oleg Denisenko, and Jerzy Ostrowski, "hnRNP K: One protein multiple processes" Bio Essays 26 p. 629-638, 2004.

Masaki Kitazono, Yuji Takebayashi, Kenji Ishitsuka, Sonshin Takao, Ayako Tani, Tatsuhiko Furukawa, Kazutaka Miyadera, Yuji Yamada, Takashi Aikou, and Shin-Ichi Akiyama, "Prevention of Hypoxia-Induced Apoptosis by the Angiogenic Factor Thymidine Phosphorylase." Biochemical and Biophysical Research Communications 253, p. 797-803(1998).

B Carpenter, M McKay, SR Dundas, LC Lawrie, C Telferr and GI Murray "Heterogeneous nuclear ribonucleoprotein K is over expressed, aberrantly localized and is associated with poor prognosis in colorectal cancer." British Journal of Cancer (2006)95, p. 921-927.

Sandra Liekensa, Annelies Bronckaers, Maria-Je'sus Pe'rez-Pe'rez, Jan Balzarini, "Targeting platelet-derived endothelial cell growth factor/thymidine phosphorylase for cancer therapy" Biochemical Pharmacology 74 (2007) p. 1555-1567.

Hiromitsu Hatakeyama, Tadishi Kondo, Kiyonaga Fujii, Yukihiro Nakanishi, Hoichi Kato, Satoshi Fukuda and Setsuo Hirohashi "Protein clusters associated with carcinogenesis, histological differentiation and nodal metastasis in esophageal cancer" Proteomics 2006, 6, p. 6300-6316.

Lih-Chyang Chen, Chuen Hsueh, Ngan-Ming Tsang, Ying Liang, Kai-Ping Chang, Sheng-Po Hao, Jau-Song Yu, and Yu-Sun Chang, Heterogeneous Ribonucleoprotein K and Thymidine Phosphorylase Are Independent Prognostic and Therapeutic Makers for Nasopharyngeal Carcinoma, Published: Jun. 15, 2008, pp. 3807-3813.

Lih-Chyang Chen, Chuen Hsueh, Ngan-Ming Tsang, Ying Liang, Kai-Ping Chang, Sheng-Po Hao, Jau-Song Yu, and Yu-Sun Chang, Heterogeneous Nuclear Ribonucleoprotein K and Thymidine Phosphorylase Are Independent Prognostic and Therapeutic Makers for Nasopharyngeal Carcinoma, Published Nov. 7, 2008.

Lih-Chyang Chen, Chuen Hsueh, and Yu-Sun Chang, Mechanistic Study for Interleukin-8 Regulation in Immune Cell-Infiltrated Nasopharyngeal Carcinoma, Published: Mar. 29, 2009.

L-C Chen, H-P Liu, H-P Li, C. Hsueh, J-S Yu, C-L Liang and Y-S Chang, Thymidine Phosphorylase MRNA Stability and Protein Levels Are Increased through ERKk-mediated Cytoplamic Accumulation of hnRNP K in Nasopharyngeal Carciinoma Cells, Published: Mar. 30, 2009, pp. 1904-1915.

* cited by examiner

*Primary Examiner* — Sean McGarry

(74) *Attorney, Agent, or Firm* — Muncy, Geissler, Olds & Lowe, PLLC

(57) ABSTRACT

The present invention discloses a TP expression-inhibiting compound and a TP expression-inhibiting siRNA sequence, wherein a siRNA sequence partially or completely complementary to the sequence of TP is used to inhibit TP expression, whereby is effectively reduced the survival rate of cancer cells in an anoxic environment.

3 Claims, 3 Drawing Sheets

TP EXPRESSION-INHIBITING COMPOUND AND SIRNA SEQUENCE THEREOF

FIELD OF THE INVENTION

The present invention relates to an RNA interferon technology, particularly to a TP expression-inhibiting compound and a siRNA sequence thereof.

DESCRIPTION OF THE RELATED ART

Thymidine phosphorylase (TP), also called PD-ECGF (Platelet-Derived Endothelial Cell Growth Factor), plays a very important role in nucleotide metabolism. TP also induces angiogenesis and metastasis. Thus, TP can inhibit apoptosis. It was reported that the product of TP metabolism 2-deoxy-D-ribose can inhibit the anoxia-induced apoptosis. It has been known that TP is over expressed in many cancers and very useful in prognosis. The over-expression of TP and the activity of enzyme can catalyze the activity of a precursor medicine of capecitabine. TP has been allowed to use in the therapy of the patients of metastatic colorectal cancer and metastatic breast cancer. The TP promoter is regulated by the transcription factors Sp1 and STAT. Besides, the stability of TP RNA is regulated by an interferon on the post-transcription level.

The Inventors found that TP is over-expressed in nasopharyngeal cancer and clinically correlates with the overall survival rate and distant metastasis. Therefore, PT can be used as a biomarker for predicting the malignancy of cancer. In the current cancer therapy technology, there is still none molecular method or medicine inhibiting the expression of TP-the over-expressing gene in breast cancer, colorectal cancer, and nasopharyngeal cancer.

SUMMARY OF THE INVENTION

The primary objective of the present invention is to provide a TP (Thymidine Phosphorylase) expression-inhibiting compound and a siRNA (small interfering RNA) sequence thereof, wherein the siRNA corresponding to TP is used to effectively inhibit TP expression and suppress the growth, metastasis and invasion of cancer.

To achieve the abovementioned objective, the present invention proposes a TP expression-inhibiting compound and a siRNA sequence thereof, wherein a siRNA is used to inhibit TP expression, and wherein a small segment of RNA having about 18-24 pieces of nucleotides matches with the mRNA (messenger RNA) of TP and then the intracellular dicer recognizes the segment of RNA, whereby the mRNA of TP is cut off, and the TP expression is inhibited.

The siRNA designed by the present invention matches with TP mRNA and has a transcribable sequence

```
GGACAAGCAUUCCACAGGGUU        (SEQ ID NO: 1)

CAGCCUCCAUUCUCAGUAAUU        (SEQ ID NO: 2)

GCAUGUGGCUGCAAGGUGCUU        (SEQ ID NO: 3)

GAGCGAAGCGGACAUCAGGUU        (SEQ ID NO: 4)
``` which can inhibit TP expression and thus can reduce the survival rate of cancer cells in an anoxic environment.

Below, the present invention is described in detail in cooperation with the attached drawings to make easily understood the objective, characteristics and accomplishments of the present invention.

DETAILED DESCRIPTION OF THE INVENTION

Figure 1A:
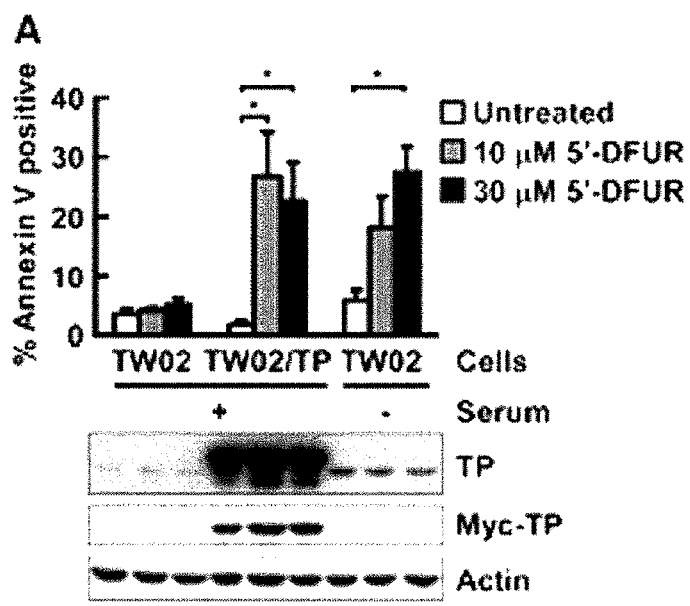
FIGS. 1A and 1B are diagrams respectively schematically showing the influence of TP expression on the cell line of nasopharyngeal cancer in a 5'-DFUR environment and an anoxic environment.

The TP (Thymidine Phosphorylase) expression-inhibiting compound and a siRNA (small interfering RNA) sequence thereof can effectively inhibit TP expression and thus can reduce the survival rate of cancer cells in an anoxic environment and can then suppress the growth of cancer cells, includes colorectal cancer, lung cancer, oral squamous cell cancer, prostate cancer, nasopharyngeal cancer. The nasopharyngeal cancer cells are used as the exemplification of the abovementioned cancer cells in the present invention.

In related experiments, the Inventors found that Protein K of ribonucleoprotein particles (hnRNP K) and the target thereof—TP are over-expressed in nasopharyngeal cancer. The abnormal hnRNP K expression and TP over-expression in cytoplasm correlates with the shorter overall survival period and the distant metastasis. A multivariate analysis shows that hnRNP K and TP in cytoplasm is the independent factor for prognosis. TP over-expression in nasopharyngeal cancer cells makes the cancer cells more sensitive to the intermediate product of capecitabine—the precursor medicine 5-fluoro-5'-deoxyuridine (5'-DFUR), which can induce the apoptosis of cancer cells. Besides, the removal of serum will increase the stability of TP and cause TP over-expression.

RT-PCR-based immunoprecipitation and the transfer of hnRNP K from nucleus to cytoplasm shows that a UMP and CMP-rich segment of TP can directly interact with hnRNP K. Therefore, inhibiting hnRNP K expression can reduce TP expression. It means that hnRNP K should be the upstream of TP. In the reaction mechanism, both the MEK inhibitor (Mitogen-activated protein/Extracellular signal-regulated Kinase) and the amino mutation of p-ERK (phosphorylated Extracellular signal-Regulated kinases) can reduce hnRNP K expression in cytoplasm. Therefore, the phosphorylation of hnRNP K by ERK maybe plays an important role in inducing TP.

Besides, the TP expression activated by hnRNP K can inhibit the anoxic apoptosis of nasopharyngeal cancer cells. In conclusion, our experiments show that ERK can induce increasing hnRNP K expression. Thus, hnRNP K is the upstream of TP, and TP is the downstream target of hnRNP K. Both hnRNP K and TP are effective indicators to prognose nasopharyngeal cancer and deserves designing new targeted-therapy medicine thereof, which should benefit cancer therapy.

Therefore, the present invention suppresses the growth, metastasis and invasion of nasopharyngeal cancer via inhibiting TP expression. The TP expression-inhibiting compound may be the nucleotide molecules of RNA or DNA, which has a sense region and an antisense region jointly forming a duplex region. The sense region and the antisense region respectively have a length of 18-30 nucleotides. The antisense region has a sequence completely or partially matching the sequence of the mRNA of TP, whereby TP expression is inhibited, and the growth, metastasis, and invasion of cancer cells is suppressed.

In other words, the TP-inhibiting siRNA contains the following sequence:

| | |
|---|---|
| GGACAACCAUUCCACAGGGUU | (SEQ ID NO: 1) |
| CAGCCUCCAUUCUCAGUAAUU | (SEQ ID NO: 2) |
| GCAUGUGGCUGCAAGGUGCUU | (SEQ ID NO: 3) |
| GAGCGAAGCGGACAUCAGGUU | (SEQ ID NO: 4) |

Below, experimental data is used to prove the efficacies of the present invention. The cell lines of nasopharyngeal cancer NPC-TW01, NPC-TW02 and NPC-TW04 were cultivated in DMEM (Dulbecco's Modified Eagle's Medium) supplemented with 10% fetal bovine serum, 100 U/ml penicillin, and 100 µg/ml streptomycin at a temperature of 37° C. in a humidified 5% $CO_2$ atmosphere. The cells are also cultivated in a serum-free DMEM, i.e. treated with a serum deprivation process. The cell lines NPC-TW02 is cultivated in DMEM supplemented with 10% fetal bovine serum, 100 U/ml penicillin, and 100 µg/ml streptomycin at 37° C. in a humidified 5% $CO_2$ atmosphere. The expression of endogenous TP can be induced by the serum deprivation processing, as shown in FIG. 1A.

Figure 1B:
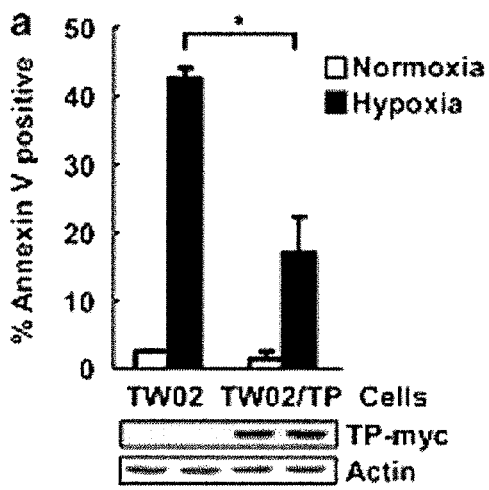

Refer to FIG. 1A and FIG. 1B. A cell line of nasopharyngeal cancer NPC-TW02/TP is established to stably express exogenous TP. First, the TP-expression carrier pcDNA3.1-PT is transfected to the cell line. Next, the cell line is screened and then cultivated in a culture solution having 500 µg/ml G418. Next is performed a cytotoxicity assay, wherein NPC-TW02 and NPC-TW02/TP are respectively processed with 5'-DFUR (Sigma-Aldrich, St. Louis, Mo., USA). Next, the cell lines are further cultivated for 72 hours. Next, the cell membranes are everted to expose phosphatidylserine. Then, phosphatidylserine is analyzed with the Vybrant® Apoptosis Assay Kit #2 (a product of Invitrogen).

Figure 2:
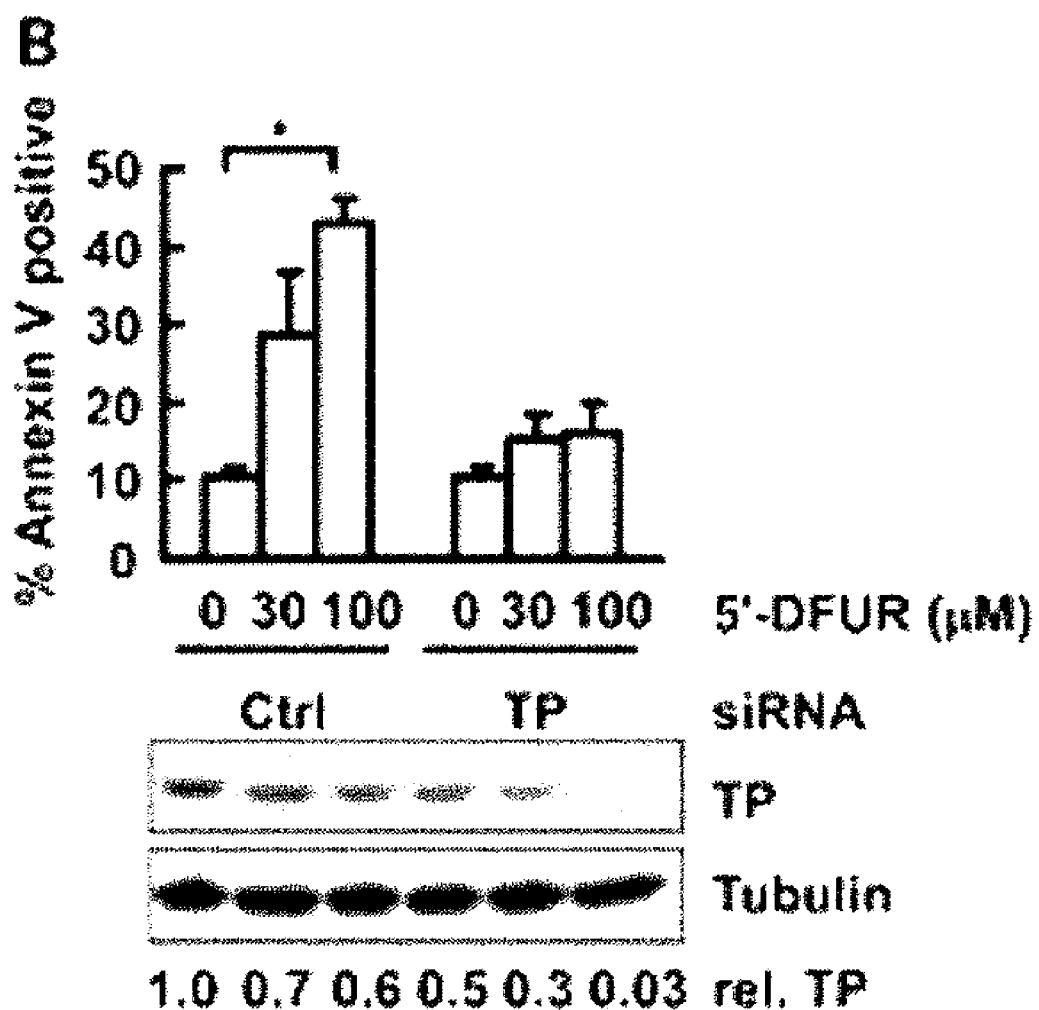
FIG. 2 is a diagram schematically showing the effect of a TP expression-inhibiting compound according to the present invention.

Firstly, $2\times10^5$ cells are taken out and washed with PBS. Next, a buffer solution (10 mM HEPES, 140 mM NaCl, 2.5 mM $CaCl_2$, pH 7.4) is used to adjust the solution to have a cell concentration of $2\times10^6$/mL. Next, 5 µl Alexa Fluor® 488 annexin V is added into 100 µl cell suspension, and then the cell suspension reacts at an ambient temperature for 15 minutes. Next, the cell specimens (10000 events) are analyzed with a flow cytometer (a product of Becton Dickinson), as shown in FIG. 3. Next is performed an anoxic experiment, wherein a six-hole culture tray planted with cells is placed in a modular incubator chamber (Billups-Rothenberg, Del Mar, Calif.), and an air having 2% $O_2$, 5% $CO_2$, and 93% $N_2$ flows through the incubator chamber with a flow rate of 20 l/min for 8 minutes. Next, the incubator chamber is sealed, and the cells are cultivated for 72 hours at a temperature of 37° C. Refer to FIG. 2. Next, the cell membranes are everted to expose phosphatidylserine. Then, phosphatidylserine is analyzed with the Vybrant® Apoptosis Assay Kit #2 (a product of Invitrogen).

Figure 3A:
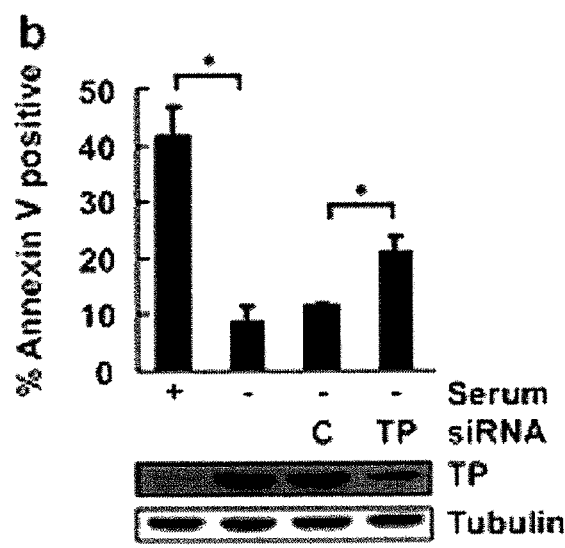
FIGS. 3A and 3B are diagrams schematically showing the effect of a TP expression-inhibiting compound according to the present invention.
Figure 3B:
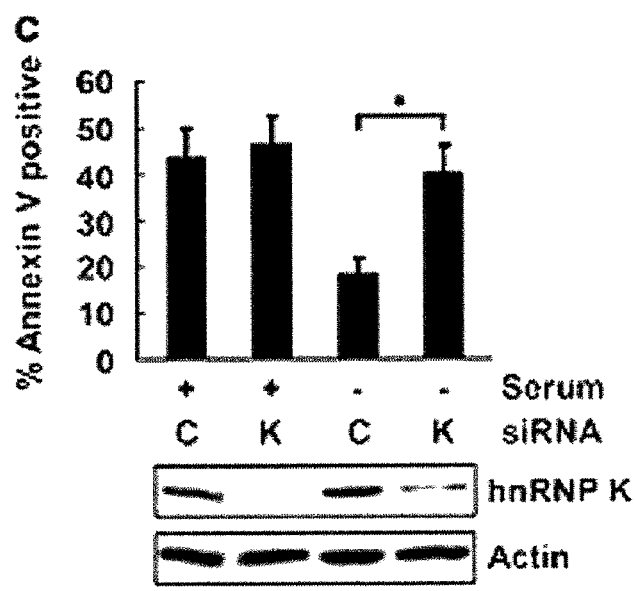

According to the operation manual, 50 µg transfection agent TransIT-TKO (a product of Mirus Bio Corporation) is used to transfect 50 nmol/l dsRNA duplexes to the cell line NPC-TW02, wherein a 21-bp hnRNP K and TP-addressing RNA duplex (SMARTpool reagents, Dharmacon, Lafayette, Colo.) and a 21-bp none-addressing RNA duplex (Research Biolabs Ayer Rajah Industrial Estate) are transfected to the cell line NPC-TW02. 24 hours later from transfection, the siRNA-containing culture solution is replaced with a serum-containing culture solution and a serum-free culture solution. Refer to FIG. 2, FIG. 3A and FIG. 3B. 48 hours later from culture solution replacement, the cells are collected to extract cell protein to examine the gene expression-inhibiting effect of the transfected RNA duplexes.

The mRNA of TP may have a sequence shown in Table. 1 (SEQ ID NO: 5).

TABLE 1

| | | | | | |
|---:|---|---|---|---|---|
| 1 | cgactgccga | gctccgccct | ccaggcggcc | ccacccgcct | gccgtcctgg ggcgccgccg |
| 61 | ccccgccgcc | ggcagtggac | cgctgtgcgc | gaaccctgaa | ccctacggtc ccgaccgcg |
| 121 | ggcgaggccg | ggtacctggg | ctgggatccg | gagcaagcgg | gcgagggcag cgccctaagc |
| 181 | aggcccggag | cgatggcagc | cttgatgacc | ccgggaaccg | gggccccacc cgcgcctggt |
| 241 | gacttctccg | gggaagggag | ccagggactt | cccgaccctt | cgccagagcc caagcagctc |
| 301 | ccggagctga | tccgcatgaa | gcgagacgga | ggccgcctga | gcgaagcgga catcagggc |
| 361 | ttcgtggccg | ctgtggtgaa | tgggagcgcg | cagggcgcac | agatcggggc catgctgatg |
| 421 | gccatccgac | ttcggggcat | ggatctggag | gagacctcgg | tgctgaccca ggccctggct |
| 481 | cagtcggac | agcagctgga | gtggccagag | gcctggcgcc | agcagcttgt ggacaagcat |
| 541 | tccacagggg | gtgtgggtga | caaggtcagc | ctggtcctcg | cacctgccct ggcggcatgt |
| 601 | ggctgcaagg | tgccaatgat | cagcggacgt | ggtctgggc | acacaggagg caccttggat |
| 661 | aagctggagt | ctattcctgg | attcaatgtc | atccagagcc | cagagcagat gcaagtgctg |
| 721 | ctggaccagg | cgggctgctg | tatcgtgggt | cagagtgagc | agctggttcc tgccgacgga |
| 781 | atcctatatg | cagccagaga | tgtgacagcc | accgtggaca | gcctgccact catcacagcc |
| 841 | tccattctca | gtaagaaact | cgtggagggg | ctgtccgctc | tggtggtgga cgttaagttc |
| 901 | ggagggccg | ccgtcttccc | caaccaggag | caggcccggg | agctggcaaa gacgctggtt |
| 961 | ggcgtgggag | ccagcctagg | gcttcgggtc | gcggcagcgc | tgaccgccat ggacaagccc |

TABLE 1-continued

```
1021 ctggtcgct gcgtgggcca cgccctggag gtggaggagg cgctgctctg catggacgcc 1081 gcaggcccgc cagacttaag ggacctggtc accacgctcg ggggcgccct gctctggctc 1141 agcggacacg cggggactca ggcccagggc gctgcccggg tggccgcggc gctggacgac 1201 ggctcggccc ttggccgctt cgagcggatg ctggcggcgc agggcgtgga tcccggtctg 1261 gcccgagccc tgtgctcggg aagtcccgca gaacgccggc agctgctgcc tcgcgcccgg 1321 gagcaggagg agctgctggc gcccgcagat ggcaccgtgg agctggtccg ggcgctgccg 1381 ctggcgctgg tgctgcacga gctcggggcc gggcgcagcc gcgctgggga gccgctccgc 1441 ctgggggtgg gcgcagagct gctggtcgac gtgggtcaga ggctgcgccg tgggaccccc 1501 tggctccgcg tgcaccggga cggccccgcg ctcagcggcc cgcagagccg cgccctgcag 1561 gaggcgctcg tactctccga ccgcgcgcca ttcgccgccc cctcgccctt cgcagagctc 1621 gttctgccgc cgcagcaata aagctccttt gccgcgaaa
```

In conclusion, the present invention proposes a TP expression-inhibiting compound and a siRNA sequence thereof, which uses an RNA interfering technology to inhibit TP expression inside cancer cells and suppress canceration, including the growth, metastasis and invasion of cancer cells.

The present invention has been demonstrated with the embodiments described above. However, they are only to exemplify the present invention but not to limit the scope of the present invention. Any equivalent modification or variation according to the spirit of the present invention is to be also included within the scope of the present invention, which is based on the claims stated below.

---

What is claimed is:

1. A thymidine phosphorylase expression-inhibiting compound, which is a nucleotide-based molecule having a sense region and an antisense region jointly forming a duplex region, wherein each of said sense region and said antisense region has a length of 18-30 nucleotides, wherein said sense region contains the nucleotide sequence of:

```
GCAUGUGGCUGCAAGGUGCUU      (SEQ ID NO: 3)
or

GAGCGAAGCGGACAUCAGGUU      (SEQ ID NO: 4)
``` and wherein said antisense region contains a sequence matching with a sequence of an mRNA of thymidine phosphorylase and inhibiting expression of thymidine phosphorylase and suppress growth, metastasis and invasion of cancer cells.

2. The thymidine phosphorylase expression-inhibiting compound of claim 1, wherein said cancer cells are selected from the group consisting of colorectal cancer cells, lung cancer cells, oral squamous cell cancer cells, prostate cancer cells, and nasopharyngeal cancer cells.

3. The thymidine phosphorylase expression-inhibiting compound of claim 1, wherein said nucleotide-based molecule is ribonucleic acid or deoxyribonucleic acid.

* * * * *

SEQUENCE LISTING

<160> NUMBER OF SEQ ID NOS: 5

<210> SEQ ID NO 1
<211> LENGTH: 21
<212> TYPE: RNA
<213> ORGANISM: Artificial Sequence
<220> FEATURE:
<223> OTHER INFORMATION: Synthetic TP-inhibiting siRNA

<400> SEQUENCE: 1
ggacaagcau uccacagggu u                                              21

<210> SEQ ID NO 2
<211> LENGTH: 21
<212> TYPE: RNA
<213> ORGANISM: Artificial Sequence
<220> FEATURE:
<223> OTHER INFORMATION: Synthetic TP-inhibiting siRNA

<400> SEQUENCE: 2
cagccuccau ucucaguaau u                                              21

<210> SEQ ID NO 3
<211> LENGTH: 21
<212> TYPE: RNA
<213> ORGANISM: Artificial Sequence
<220> FEATURE:
<223> OTHER INFORMATION: Synthetic TP-inhibiting siRNA

<400> SEQUENCE: 3

| | |
|---|---|
| gcauguggcu gcaaggugcu u | 21 |

<210> SEQ ID NO 4
<211> LENGTH: 21
<212> TYPE: RNA
<213> ORGANISM: Artificial Sequence
<220> FEATURE:
<223> OTHER INFORMATION: Synthetic TP-inhibiting siRNA

<400> SEQUENCE: 4

| | |
|---|---|
| gagcgaagcg gacaucaggu u | 21 |

<210> SEQ ID NO 5
<211> LENGTH: 1659
<212> TYPE: DNA
<213> ORGANISM: Artificial Sequence
<220> FEATURE:
<223> OTHER INFORMATION: Chemically synthesized mRNA of thymidine phosphorylase (TP)

<400> SEQUENCE: 5

| | |
|---|---|
| cgactgccga gctccgccct ccaggcggcc ccacccgcct gccgtcctgg ggcgccgccg | 60 |
| ccccgccgcc ggcagtggac cgctgtgcgc gaaccctgaa ccctacggtc ccgacccgcg | 120 |
| ggcgaggccg ggtacctggg ctgggatccg gagcaagcgg gcgagggcag cgccctaagc | 180 |
| aggcccggag cgatggcagc cttgatgacc ccgggaaccg ggcccccacc cgcgcctggt | 240 |
| gacttctccg gggaagggag ccagggactt cccgacccct cgccagagcc caagcagctc | 300 |
| ccggagctga tccgcatgaa gcgagacgga ggccgcctga gcgaagcgga catcaggggc | 360 |
| ttcgtggccg ctgtggtgaa tgggagcgcg cagggcgcac agatcggggc catgctgatg | 420 |
| gccatccgac ttcggggcat ggatctggag gagacctcgg tgctgaccca ggccctggct | 480 |
| cagtcgggac agcagctgga gtggccagag gcctggcgcc agcagcttgt ggacaagcat | 540 |
| tccacagggg gtgtgggtga caaggtcagc ctggtcctcg cacctgccct gcggcatgt | 600 |
| ggctgcaagg tgccaatgat cagcggacgt ggtctggggc acacaggagg caccttggat | 660 |
| aagctggagt ctattcctgg attcaatgtc atccagagcc agagcagat gcaagtgctg | 720 |
| ctggaccagg cgggctgctg tatcgtgggt cagagtgagc agctggttcc tgcggacgga | 780 |
| atcctatatg cagccagaga tgtgacagcc accgtggaca gcctgccact catcacagcc | 840 |
| tccattctca gtaagaaact cgtggagggg ctgtccgctc tggtggtgga cgttaagttc | 900 |
| ggagggccg ccgtcttccc caaccaggag caggcccggg agctggcaaa gacgctggtt | 960 |
| ggcgtgggag ccagcctagg gcttcgggtc gcggcagcgc tgaccgccat ggacaagccc | 1020 |
| ctgggtcgct gcgtgggcca cgccctggag gtggaggagg cgctgctctg catggacggc | 1080 |
| gcaggcccgc cagacttaag ggacctggtc accacgctcg ggggcgccct gctctggctc | 1140 |
| agcggacacg cggggactca ggcccagggc gctgcccggg tggccgcggc gctggacgac | 1200 |
| ggctcggccc ttggccgctt cgagcggatg ctgcggcgc agggcgtgga tcccggtctg | 1260 |
| gcccgagccc tgtgctcggg aagtcccgca gaacgccggc agctgctgcc tcgcgcccgg | 1320 |
| gagcaggagg agctgctggc gcccgcagat ggcaccgtgg agctggtccg ggcgctgccg | 1380 |
| ctggcgctgg tgctgcacga gctcggggcc gggcgcagcc gcgctgggga gccgctccgc | 1440 |

```
ctgggggtgg gcgcagagct gctggtcgac gtgggtcaga ggctgcgccg tgggaccccc    1500
tggctccgcg tgcaccggga cggccccgcg ctcagcggcc cgcagagccg cgccctgcag    1560
gaggcgctcg tactctccga ccgcgcgcca ttcgccgccc cctcgccctt cgcagagctc    1620
gttctgccgc cgcagcaata aagctccttt gccgcgaaa                           1659
```